(12) United States Patent
Hendrick (10) Patent No.: US 9,421,035 B2
(45) Date of Patent: Aug. 23, 2016

(54) METHOD FOR LEAD TIP REMOVAL USING A STABILIZATION DEVICE

(71) Applicant: The Spectranetics Corporation, Colorado Springs, CO (US)

(72) Inventor: Brandon Thomas Hendrick, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 350 days.

(21) Appl. No.: 13/801,267

(22) Filed: Mar. 13, 2013

(65) Prior Publication Data
US 2014/0276926 A1 Sep. 18, 2014

(51) Int. Cl.
*A61N 1/05* (2006.01)
*A61B 17/50* (2006.01)
*A61B 17/34* (2006.01)

(52) U.S. Cl.
CPC .......... *A61B 17/3468* (2013.01); *A61N 1/0573* (2013.01); *A61B 17/50* (2013.01); *A61N 1/056* (2013.01); *A61N 1/0587* (2013.01); *A61N 2001/0578* (2013.01)

(58) Field of Classification Search
CPC ..... A61N 1/056; A61N 1/059; A61N 1/0592; A61N 2001/058; A61N 2001/0573; A61N 2001/0578; A61N 2001/0587; A61M 25/04; A61B 17/3468; A61B 17/10; A61B 17/128; A61B 2017/0411; A61B 2017/049; A61B 17/50
USPC ....................................... 606/129; 254/21–25
See application file for complete search history.

(56) References Cited

U.S. PATENT DOCUMENTS

| 4,574,800 | A | * | 3/1986 | Peers-Trevarton | 606/1 |
| 4,582,056 | A | * | 4/1986 | McCorkle, Jr. | 606/1 |
| 5,423,806 | A | * | 6/1995 | Dale et al. | 606/15 |
| 5,549,615 | A | * | 8/1996 | Hocherl et al. | 606/108 |
| 5,556,424 | A | * | 9/1996 | Hocherl et al. | 607/116 |
| 5,779,715 | A | * | 7/1998 | Tu | 606/108 |
| 5,807,399 | A | * | 9/1998 | Laske et al. | 607/126 |
| 5,980,515 | A | * | 11/1999 | Tu | 606/41 |
| 5,984,946 | A | * | 11/1999 | Gupta | 606/194 |
| 6,122,552 | A | * | 9/2000 | Tockman et al. | 607/116 |

(Continued)

OTHER PUBLICATIONS

Love et al, Recommendations for extraction of chronically implanted transvenous pacing and defibrillator leads: indications, facilities, training. PACE, vol. 23, 2000, pp. 544-551.*

(Continued)

*Primary Examiner* — Christopher L Templeton
(74) *Attorney, Agent, or Firm* — Faegre Baker Daniels LLP (57) ABSTRACT

Lead tip removal is accomplished by first stabilizing an area around the lead tip attachment site in the heart wall. A balloon located at the tip of the lead when inflated expands substantially perpendicular to the lead, stabilizing the area around the lead tip. Upon further inflation, the balloon expands substantially parallel with the lead, causing the lead tip to pull away from the heart wall. In another embodiment, a sheath is inserted over the lead and advanced to the heart wall. A passive or active stabilization device is attached to the sheath tip to stabilize the area around the lead tip. In another embodiment, a balloon is located at the tip of the sheath that, when inflated, expands substantially perpendicular to the lead, stabilizing the area around the lead tip. The lead tip is removed with less force due to the stabilization provided to the lead tip area.

6 Claims, 6 Drawing Sheets

(56) References Cited

U.S. PATENT DOCUMENTS

| | | | |
|---|---|---|---|
| 7,993,359 B1* | 8/2011 | Atwell et al. | 606/170 |
| 2002/0007204 A1* | 1/2002 | Goode | 607/115 |
| 2002/0165536 A1* | 11/2002 | Kelley et al. | 606/41 |
| 2003/0060799 A1* | 3/2003 | Arenberg et al. | 604/514 |
| 2004/0010281 A1* | 1/2004 | Mika | 606/194 |
| 2004/0059348 A1* | 3/2004 | Geske et al. | 606/129 |
| 2004/0199236 A1* | 10/2004 | Laske et al. | 607/129 |
| 2004/0215139 A1* | 10/2004 | Cohen | 604/95.04 |
| 2005/0065419 A1* | 3/2005 | Partridge et al. | 600/374 |
| 2005/0182465 A1* | 8/2005 | Ness | 607/116 |
| 2006/0089694 A1* | 4/2006 | Zhang et al. | 607/122 |
| 2006/0111739 A1* | 5/2006 | Staufer et al. | 606/192 |
| 2007/0149995 A1* | 6/2007 | Quinn et al. | 606/194 |
| 2008/0071341 A1* | 3/2008 | Goode et al. | 607/122 |
| 2009/0234367 A1* | 9/2009 | Verma | A61N 1/05 606/129 |
| 2010/0198229 A1* | 8/2010 | Olomutzki | A61B 17/32053 606/129 |
| 2010/0228262 A1* | 9/2010 | Cully et al. | 606/129 |
| 2011/0106099 A1* | 5/2011 | Duffy et al. | 606/129 |
| 2011/0178543 A1* | 7/2011 | Chin | A61B 17/50 606/190 |
| 2012/0323252 A1* | 12/2012 | Booker | 606/129 |

OTHER PUBLICATIONS

Fearnot et al, Intravascular lead extraction using locking stylets, sheaths, and other techniques, 1990, PACE vol. 13, pp. 1864-1970.*

Byrd et al, Clinical Study of the laser sheath for lead extraction: the total experience in the United States, PACE vol. 24, No. 5, 2002, pp. 804-808.*

Nakamoto et al, Intravascular extraction of permanent pacemaker leads, Surg Today, (2002) 32:947-950.*

* cited by examiner

METHOD FOR LEAD TIP REMOVAL USING A STABILIZATION DEVICE

FIELD

The disclosure relates generally to lead tip removal and particularly to a stabilization device for assisted lead tip removal.

BACKGROUND

Figure 1A:
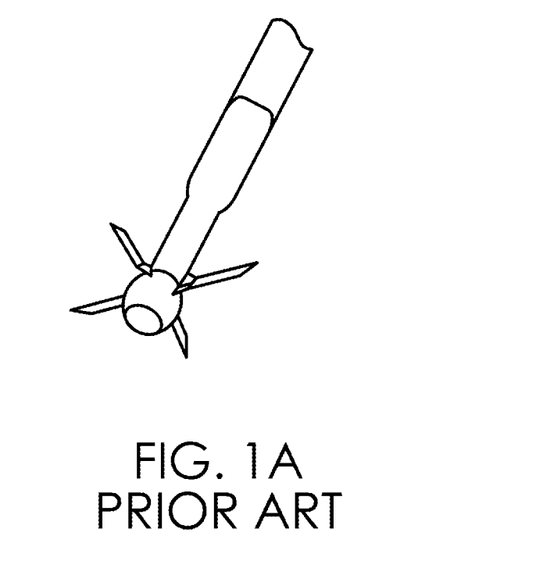
FIGS. 1A and 1B show two major types of lead tips as known in the prior art.
Figure 1B:
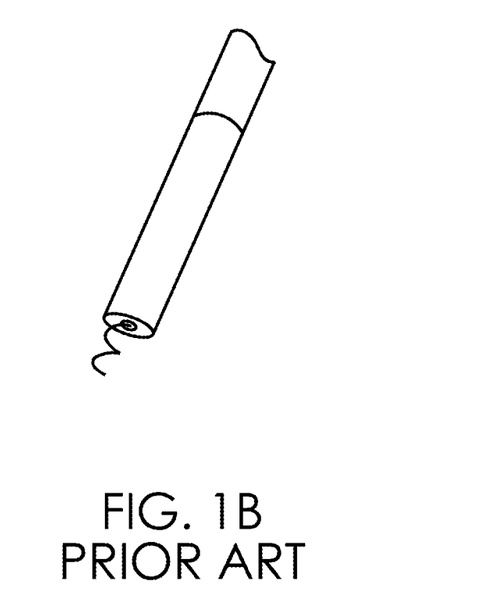

A lead is a special wire that delivers energy from a device, such as a pacemaker or implantable cardioverter defibrillator (ICD), to the heart muscle. One major type of lead tip has a small helix screw at the end (see FIG. 1B) in order to remain attached to the heart muscle, and is referred to as an active-fixation lead. Another major type of lead tip is referred to as a passive fixation lead which has soft "tines" at the tip of the lead (see FIG. 1A). The small plastic tines become passively "stuck" to the muscle in the heart and subsequent growth of scar tissue. The body's natural healing process typically forms scar tissue along the lead and at its tip within a few months of implantation, which fastens it even more securely in the patient's body. Leads usually last longer than the batteries that power the device to which they are attached.

Occasionally, however, these leads have to be removed, or extracted, even though they are designed to be implanted permanently in the body. Device infection is the most common reason for lead extraction. It is usually impossible to cure the infection without completely removing all hardware from the body if any part of the system becomes infected. This requires removal of the device from the chest wall, as well as removal of all leads from the veins and heart.

Sometimes a lead fails to work properly (e.g., due to a break in the metal wire or surrounding insulation) and is another reason requiring lead extraction. A less common reason for lead extraction is a mechanical lead failure, such as a protruding wire, that could be dangerous to the patient.

Figure 2:
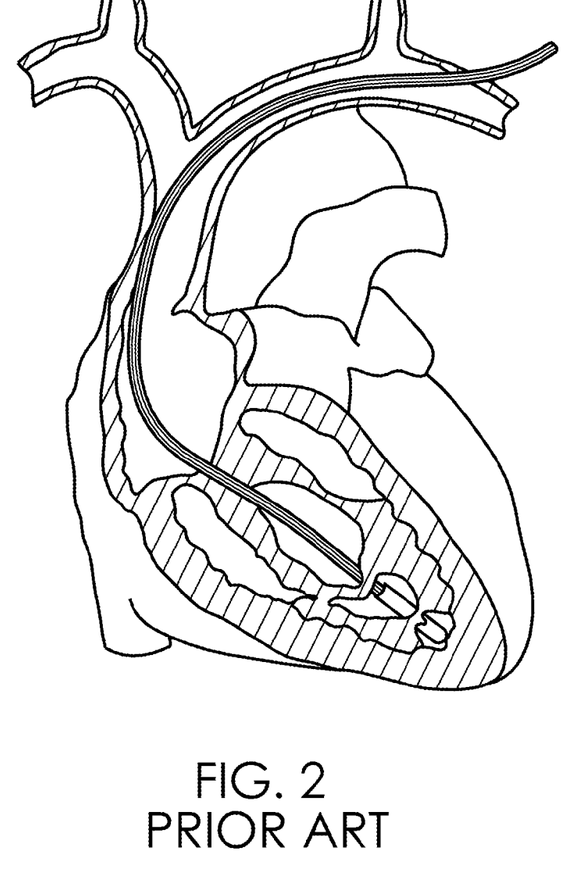
FIG. 2 shows a partial cross-section view of a lead placed within a heart as known in the prior art.

Leads run a fairly long course from the device, through the veins, and into the heart (see FIG. 2). Scar tissue may form at multiple sites along the lead due to the body's natural healing process. This scar tissue can create strong attachments of the lead to the wall of a blood vessel or a wall of a heart chamber. Freeing a lead from these attachments requires considerable skill and experience and is considered to be more difficult and risky than implanting the lead in the first place. Leads can be extracted from an access point located in the shoulder area or the leg area. Specialized tools are used to remove pacemaker and ICD leads from the inside of the heart. The most common approach follows the course of the lead through the subclavian vein under the patient's shoulder.

Figure 3:
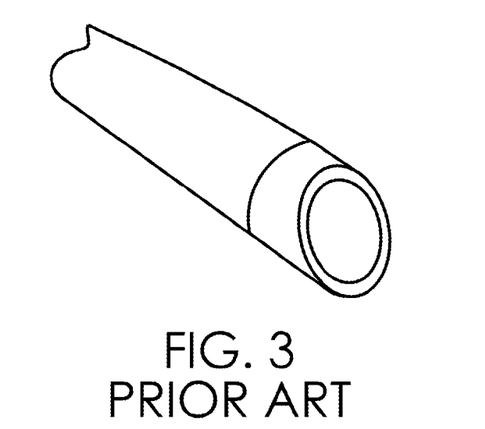
FIG. 3 shows a power sheath with ring of fiber optics that delivers laser energy at the tip as known in the prior art.

Current technologies for lead extraction utilize power sheaths, which deliver various forms of energy to the tip of the sheath, as well as mechanical cutter and dilation sheaths. As the sheath is pushed over the lead and advances to an area of scar tissue attachment, the operator can activate the sheath's cutting source functionality (energy, mechanical, dilation) to cut, dilate, heat, or vaporize the scar tissue. This has the effect of freeing the lead from its attachment points, allowing the lead to be removed with much less force. The lead can be pulled out of the body safely once the entire lead is freed from scar tissue attachments. One type of power sheath uses electro-cautery, similar to what is used to cut through tissue in surgery. Another type of power sheath has a ring of fiber optics that delivers laser energy at its tip (see FIG. 3). The lasers, when activated, vaporize water molecules in the scar tissue approximately within one mm of the tip. This allows the sheath to be passed slowly over the entire lead all the way to the heart, after which, the lead can be removed through the lumen of the sheath.

However, during some procedures, the tip of the power sheath is not adequate to provide the stabilization necessary for effective tip removal, which may cause an excessive amount of damage to the heat wall. Each time the lead is separated from scar tissue, there is a small chance of tearing the surrounding blood vessel or perforating the heart, which can result in major bleeding in the chest or around the heart. Thus, there is a need in the art for a better way to stabilize the area around the lead tip so that damage to the heart is minimized when removing the lead tip.

SUMMARY

These and other needs are addressed by the various aspects, embodiments, and configurations of the present disclosure. The disclosure is generally directed to the use of stabilization devices to assist in lead tip removal.

A method, according to the disclosure, can assist in performing lead tip removal by the steps of:

(a) inserting a sheath over a lead and advancing the sheath to a lead tip attached to a heart wall;

(b) stabilizing an area around the heart wall where the lead tip is attached with a stabilization device located at a sheath tip; and (c) removing the lead tip from the heart wall, wherein less force is required to remove the lead tip from the heart wall due to the stabilization provided to the area around the heart wall by the stabilization device.

A power source in the tip of the sheath can cut away any scar tissue at the heart wall site of the lead tip prior to removing the lead tip. Also, a lead locking device may be inserted in the lumen of the lead prior to lead tip removal and subsequent removal of the entire lead out of the patient's body.

A stabilization device for assisting in lead tip removal, according to this disclosure, can include:

a sheath; and a stabilization device attached to a sheath tip of the sheath, wherein the stabilization device stabilizes an area around a heart wall where the lead tip is attached;

wherein less force is required to remove the lead tip from the heart wall due to the stabilization provided to the area around the heart wall by the stabilization device.

The stabilization device may provide for active fixation or passive fixation of the sheath tip, and may also be a balloon.

Another method, according to the disclosure, can assist in performing lead tip removal by the steps of:

(a) stabilizing an area around the heart wall where the lead tip is attached with a balloon located at the lead tip by inflating the balloon causing the balloon to expand substantially perpendicular to the lead; and (b) removing the lead tip from the heart wall, wherein less force is required to remove the lead tip from the heart wall due to the stabilization provided to the area around the heart wall by the stabilization device.

A power source located in the tip of a sheath that is inserted over the lead can first be used to cut away any scar tissue along the lead path and at the heart wall site where the lead tip is secured prior to removing the lead tip. Also, a lead locking device may be inserted in the lumen of the lead prior to lead removal.

Another stabilization device for assisting in lead tip removal, according to this disclosure, can include:

a stabilization device attached to the lead tip of a lead, wherein the stabilization device stabilizes an area around a heart wall where the lead tip is attached;

wherein less force is required to remove the lead tip from the heart wall due to the stabilization provided to the area around the heart wall by the stabilization device.

The present disclosure can provide a number of advantages depending on the particular configuration. In one procedure, the sheath inserted over the lead has a stabilization device at the sheath tip that has either active (helix screw) or passive (soft tines) fixation functionality. This fixes the end of the sheath into the heart wall and provides fraction for lead tip removal.

In another procedure, the sheath inserted over the lead utilizes a balloon at the sheath tip for the stabilization device. The balloon expands and contacts a larger surface area of the heart wall around the lead tip to prevent heart wall injury by distributing the concentrated forces over the larger contact area.

In another procedure, the stabilization device, such as a balloon, is attached to the lead tip and remains inactive until such time as the lead needs to be removed. To remove the lead, the balloon is inflated, stabilizing the area around the lead tip. The balloon can then be further inflated to slowly provide forces to remove the lead tip (having active or passive fixation features) from the heart wall at the site of the fixation, rather than from pulling on the proximal end of the lead.

In another procedure, the stabilization device, such as a balloon, is attached to a sheath tip. A clamp is also attached near the sheath tip and locks onto the distal end of the lead. When the lead and sheath tip are locked together, the balloon at the sheath tip expands against the heart wall to provide the forces needed to remove the lead tip (having active or passive fixation features) from the heart wall at the site of the fixation, rather than from pulling on the proximal end of the lead.

These and other advantages will be apparent from the disclosure of the aspects, embodiments, and configurations contained herein. Stabilizing the area around the lead tip with the stabilization device provides a traction force opposite to the force that pulls the lead out. The stabilization device disperses the traction force over a larger surface area, thereby reducing the possibility of pulling plugs of tissue from the heart wall when the lead tip is removed. Attaching the stabilization device to the lead itself, which remains inactive until needed, may speed up the time it takes to remove a lead.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B, and C together. When each one of A, B, and C in the above expressions refers to an element, such as X, Y, and Z, or class of elements, such as $X_1$—$X_n$, $Y_1$—$Y_m$, and $Z_1$—$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

In a typical lead removal procedure, the lead or leads are prepared by removing them from the pacemaker or ICD device and cutting off the ends. If the distal tip of the lead is a helix type tip (see FIG. 1B), the proximal end may be gripped with a tool and rotated a few revolutions in the direction required, typically counterclockwise, to unscrew the helix tip from the heart wall. Next, a lead locking device is inserted into the lumen of the lead and advanced to the tip of the lead. Next, the lead locking device is activated, expanding the lead locking device within the lead lumen in order to frictionally engage with the lead throughout its entire length. Next, a power sheath is loaded over the lead/lead locking device and is advanced toward the heart (see FIGS. 2 and 3). When any scar tissue attachment area is encountered along the way, the power sheath is activated (heat or laser, etc.) to cut through the scar tissue. The power sheath is advanced until it cuts through the scar tissue present at the heart wall and brought to bear pressure against the heart wall. With the tip of the power sheath held steady against the heart wall, the lead locking device is pulled by its proximal end to remove the lead tip from the heart wall, and then further pulled until the lead/lead locking device is completely pulled out of the body from within the lumen of the power sheath. However, as described above, such procedures may lack the stabilization necessary to prevent damage to the heart upon pulling the lead tip from the heart wall.

Figure 4A:
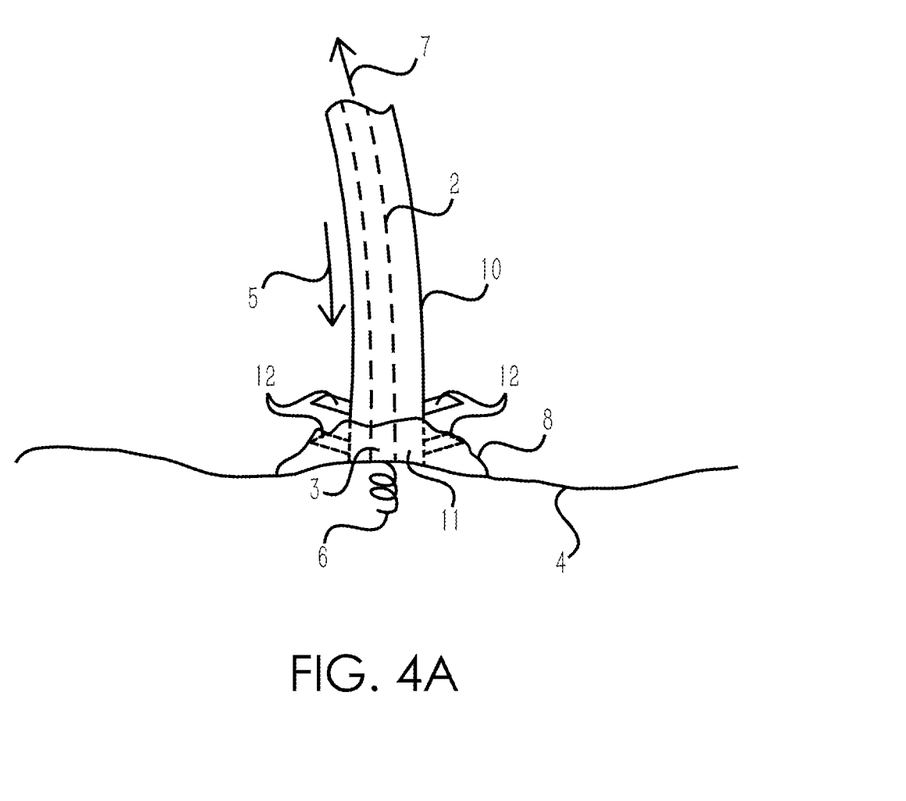
FIG. 4A shows a view of an embodiment of a sheath with a stabilization device on the end for lead tip removal.

Referring now to the Figures, like reference numerals and names refer to structurally and/or functionally similar elements thereof, and if objects depicted in the figures that are covered by another object, as well as the tag line for the element number thereto, may be shown in dashed lines. FIG. 4A shows a view of an embodiment of a sheath with a stabilization device on the end for lead tip removal. Referring now to FIG. 4A, lead 2 is secured to heart wall 4 with helix screw 6 located at lead tip 3. Scar tissue 8 has built up over time around lead tip 3. Sheath 10 has been advanced over lead 2 until it has reached heart wall 4. In one embodiment, a power sheath (see FIG. 3) has first been used to cut through scar tissue along the lead path and to cut through scar tissue 8 at lead tip 3. The power sheath is withdrawn and Sheath 10 is advanced over lead 2 until it has reached heart wall 4. In another embodiment, Sheath 10 is also a power sheath.

In either case (power sheath or non-power sheath), Sheath 10 has a stabilization device made of a plurality of Tines 12, typically made of soft plastic, and located at sheath tip 11. As Sheath 10 is advanced against heart wall 4, some of the Tines 12 engage with scar tissue 8 and any other tissue present in the area. This engagement helps stabilize sheath tip 11 of Sheath 10 against heart wall 4 and helps stabilize the area of heart wall 4 surrounding lead tip 3. The constant pressure applied to Sheath 10 against heart wall 4 provides a fraction area of force in the direction indicated by arrow 5 that is opposite the force applied to the proximal end of lead 2 in the direction indicated by arrow 7. As described above, a lead locking device (not shown in FIG. 4A) may be inserted into the lumen of lead 2 and activated. The lead locking device is pulled by its proximal end. Lead tip 3 is thus pulled free from heart wall 4. Due to the cutting of scar tissue 8, the force applied to heart wall 4 by sheath tip 11 of sheath 10, and the stabilization achieved at heart wall 4 around lead tip 3 by Tines 12 located at sheath tip 11, lead tip 3 is removed from heart wall 4 with less force than otherwise would be required, thus reducing the likelihood of damage to heart wall 4 at the attachment site of lead tip 3.

Figure 4B:
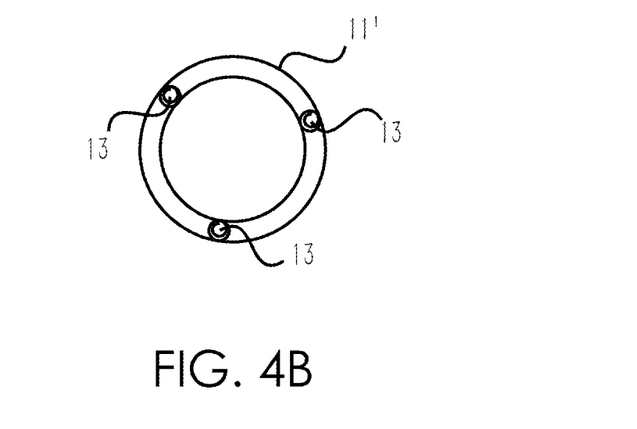
FIG. 4B shows an end view of an alternate stabilization device for the sheath.

FIG. 4B shows an end view of alternate stabilization device for the sheath. Referring now to FIG. 4B, a stabilization device of one or more helix screws 13, similar to helix screw 6 of lead 2, may be positioned around the perimeter of sheath tip 11', and are typically initially retracted within sheath tip 11'. Three helix screws 13 are shown in FIG. 4B but fewer or more helix screws 13 may be used. Three helix screws 13 achieve a very good stabilization effect. As sheath tip 11' is engaged with heart wall 4, the plurality of helix screws 13 are screwed into heart wall 4. As described above, this engagement helps stabilize sheath tip 11' against heart wall 4 and helps secure the area of heart wall 4 surrounding lead tip 3. After lead tip 3 is removed, helix screws 13 are unscrewed and retracted within sheath tip 11' of sheath 10, and sheath 10 along with lead 2 are then removed.

Figure 5:
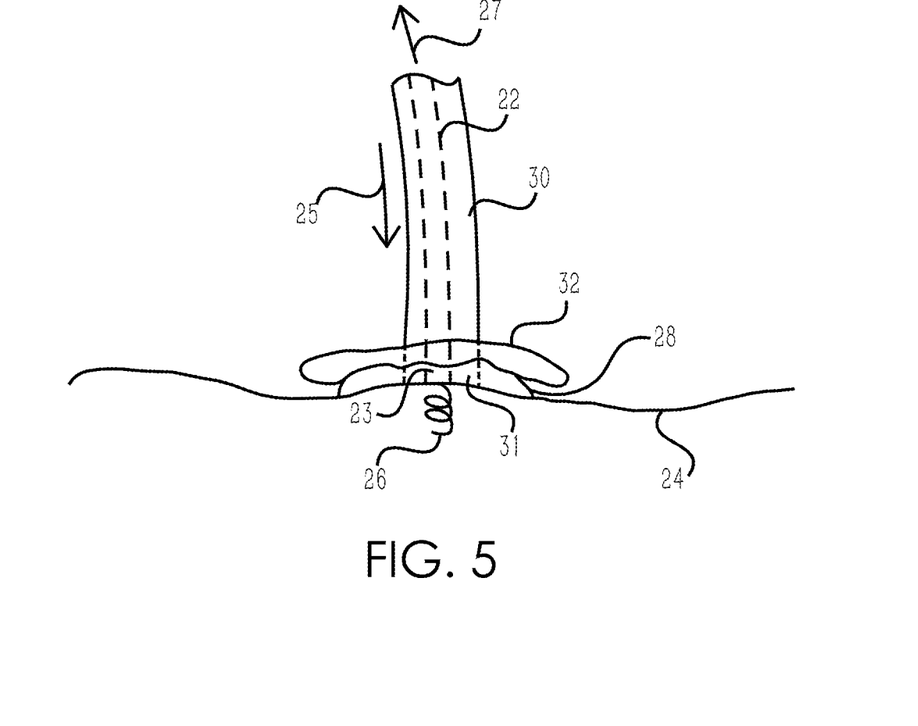
FIG. 5 shows a view of another embodiment of a sheath having a stabilization device on the end to provide more surface area to push against for lead tip removal.

FIG. 5 shows a view of another embodiment of a sheath having a stabilization device on the end to provide more surface area to push against for lead tip removal. Referring now to FIG. 5, lead 22 is secured to heart wall 24 with helix screw 26 located at lead tip 23. Scar tissue 28 has built up over time around lead tip 23. Sheath 30 has been advanced over lead 22 until it has reached heart wall 24. In one embodiment, a power sheath (see FIG. 3) has first been used to cut through scar tissue along the lead path and to cut through scar tissue 28 at lead tip 23. The power sheath is withdrawn and sheath 30 is advanced over lead 22 until it has reached heart wall 24. In another embodiment, sheath 30 is also a power sheath.

In either case (power sheath or non-power sheath), sheath 30 has an expandable member, such as balloon 32, located at sheath tip 31. Other types of expandable members beside balloon 32 may be used, such as compressed flat wires, expanded meshes, and unraveling braids/coils. As sheath 30 is advanced toward heart wall 24, balloon 32 is inflated and spreads out substantially perpendicular to sheath 30 at sheath tip 31. Sheath tip 31 presses against and applies force to balloon 32. Balloon 32 engages with scar tissue 28 and depresses it against heart wall 24. This engagement helps stabilize sheath tip 31 of sheath 30 against balloon 32 and heart wall 24 and helps secure the area of heart wall 24 surrounding lead tip 23. The constant pressure applied to heart wall 24 provides a traction area of force in the direction indicated by arrow 25 that is opposite the force applied to the proximal end of lead 22 in the direction indicated by arrow 27. As described above, a lead locking device (not shown in FIG. 5) may be inserted into the lumen of lead 22 and activated. The lead locking device is pulled by its proximal end. Lead tip 23 is thus pulled free from heart wall 24. Due to the cutting of scar tissue 28, the force applied to heart wall 24 by sheath tip 31 of sheath 30, and the stabilization achieved at heart wall 24 around lead tip 23 by balloon 32 and sheath tip 31, lead tip 23 is removed from heart wall 24 with less force than otherwise would be required, thus reducing the likelihood of damage to heart wall 24 at the attachment site of lead tip 23.

Figure 6:
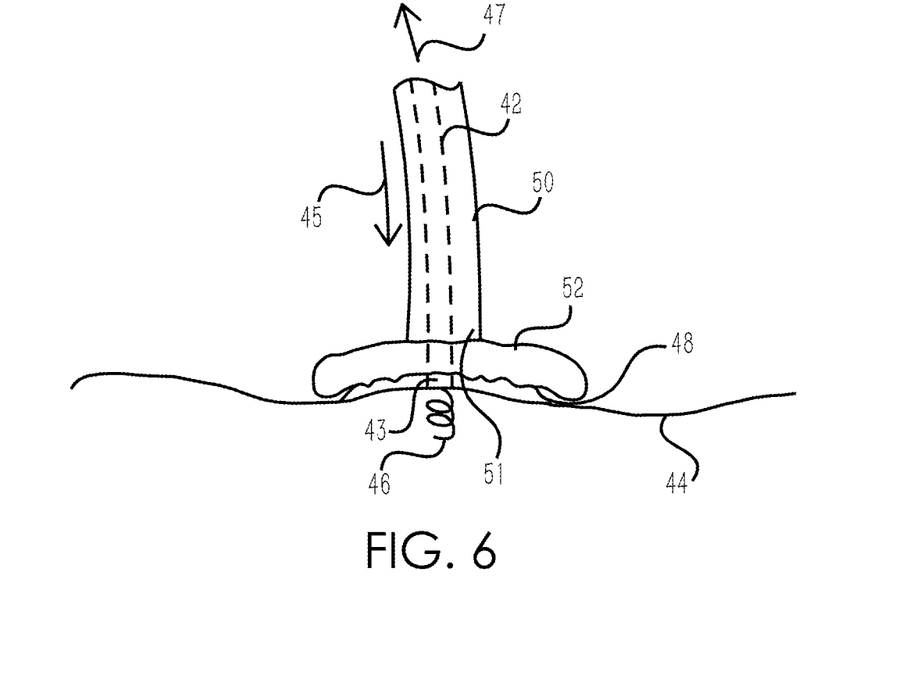
FIG. 6 shows a view of another embodiment of a lead tip having a stabilization device on the end to provide more surface area to push against for lead tip removal.

FIG. 6 shows a view of another embodiment of a lead tip having a stabilization device on the end to provide more surface area to push against for lead tip removal. Referring now to FIG. 6, lead 42 is secured to heart wall 44 with helix screw 46 located at lead tip 43. Scar tissue 48 has built up over time around lead tip 43. Sheath 50 has been advanced over lead 42 until it has reached heart wall 44. In one embodiment, a power sheath (see FIG. 3) has first been used to cut through scar tissue along the lead path and to cut through scar tissue 48 at lead tip 43. The power sheath is withdrawn. In another embodiment, sheath 50 is also a power sheath. After cutting scar tissue 48 at lead tip 43, sheath 50 is retracted a short distance over lead 42 from heart wall 44 (not shown in FIG. 6).

Lead 42 has a balloon 52 located at lead tip 43. Balloon 52 is inflated and spreads out substantially perpendicular to lead 42 at lead tip 43. Sheath 50 is then advanced against balloon 52 which may further depress scar tissue 48 against heart wall 44. This engagement helps stabilize lead tip 43 of lead 42 against heart wall 44 and helps secure the area of heart wall 44 surrounding lead tip 43. The constant pressure applied by sheath 50 against balloon 52 and heart wall 44 provides a traction area of force in the direction indicated by arrow 45 that is opposite the force applied to the proximal end of lead 42 in the direction indicated by arrow 47. As described above, a lead locking device (not shown in FIG. 6) may be inserted into the lumen of lead 42 and activated. The lead locking device is pulled by its proximal end. Lead tip 43 is thus pulled free from heart wall 44. Due to the cutting of scar tissue 48, the force applied to heart wall 44 by sheath tip 51 of sheath 50, and the stabilization achieved at heart wall 44 around lead tip 43 by balloon 52 located at lead tip 43, lead tip 43 is removed from heart wall 44 with less force than otherwise would be required, thus reducing the likelihood of damage to heart wall 44 at the attachment site of lead tip 43.

Figure 7A:
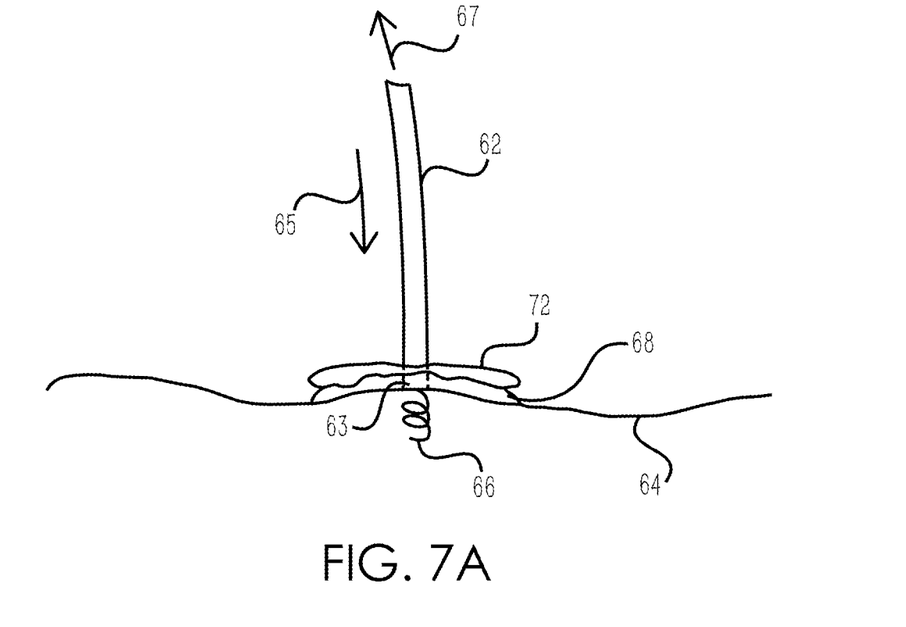
FIGS. 7A and 7B show a view of another embodiment of a lead tip having a stabilization device on the end to provide more surface area to push against for lead tip removal.
Figure 7B:
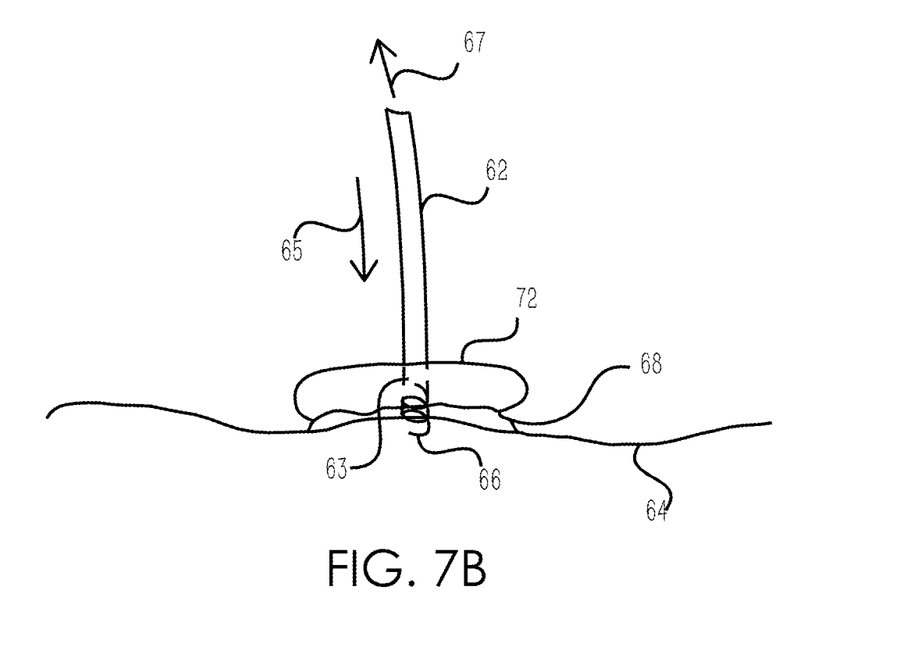

FIGS. 7A and 7B show a view of another embodiment of a lead tip having a stabilization device on the end to provide more surface area to push against for lead tip removal. Referring now to FIGS. 7A and 7B, lead 62 is secured to heart wall 64 with helix screw 66 located at lead tip 63. Scar tissue 68 has built up over time around lead tip 63. In one embodiment, a power sheath (see FIG. 3) has first been used to cut through scar tissue along the lead path. The power sheath is withdrawn.

Lead 62 has a balloon 72 located at lead tip 63. Balloon 72 is partially inflated and spreads out substantially perpendicular to lead 62 at lead tip 63 as shown in FIG. 7A. Next, as shown in FIG. 7B, balloon 72 is gradually inflated to a higher pressure, causing balloon 72 to expand in the direction indicated by arrow 67 that is substantially parallel to lead 62. This causes lead tip 63 to pull away from heart wall 64. Balloon 72 engages with scar tissue 68 and depresses it against heart wall 64. The constant pressure applied by balloon 72 against heart wall 64 provides a traction area of force in the direction indicated by arrow 65 that is opposite the force applied to lead tip 63 of lead 62 in the direction indicated by arrow 67. Due to the cutting of scar tissue 68, and the stabilization achieved by balloon 72 to heart wall 64 around lead tip 63, lead tip 63 is removed with less force than otherwise would be required, thus reducing the likelihood of damage to heart wall 64.

Figure 8A:
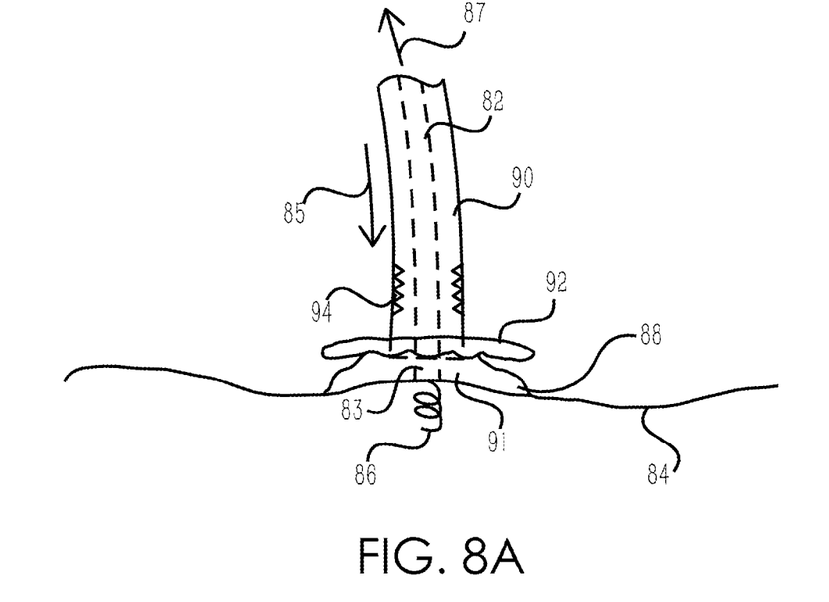
FIGS. 8A and 8B show a view of another embodiment of a sheath having a clamp and a stabilization device on the end to isolate the force at the distal end of the lead for lead tip removal.
Figure 8B:
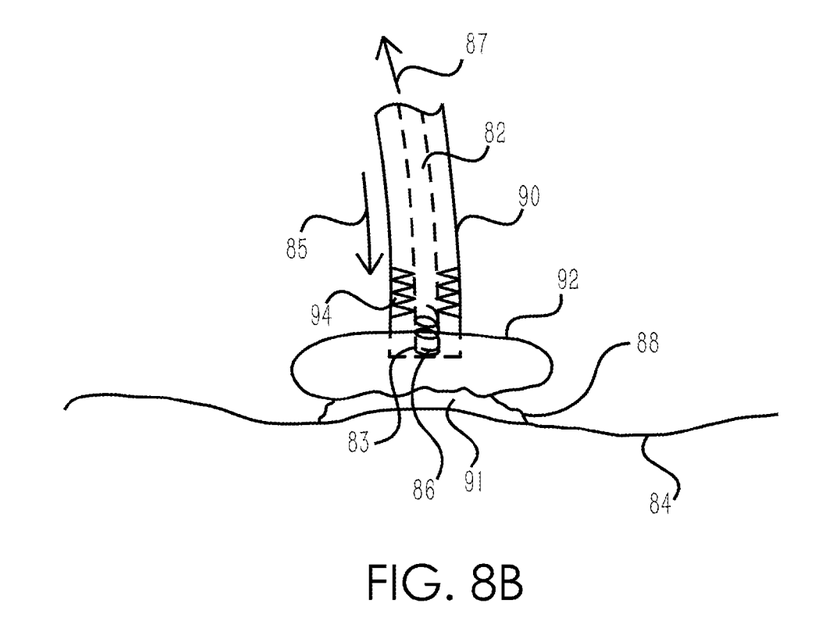

FIGS. 8A and 8B show a view of another embodiment of a sheath having a clamp and a stabilization device on the end to isolate the force at the distal end of the lead for lead tip removal. Referring now to FIGS. 8A and 8B, lead 82 is secured to heart wall 84 with helix screw 86 located at lead tip 83. Scar tissue 88 has built up over time around lead tip 83. Sheath 90 has been advanced over lead 82 until it has reached heart wall 84. In one embodiment, a power sheath (see FIG. 3) has first been used to cut through scar tissue along the lead path and to cut through scar tissue 88 at lead tip 83. The power sheath is withdrawn and sheath 90 is advanced over lead 82 until it has reached heart wall 84. In another embodiment, sheath 90 is also a power sheath.

In either case (power sheath or non-power sheath), sheath 90 has a balloon 92 located at sheath tip 91. Sheath 90 is advanced against heart wall 84 and clamp 94 internal to sheath 90 near sheath tip 91 (shown unengaged with lead 82 in FIG. 8A) is engaged with lead 82 (as shown in FIG. 8B) locking Sheath 90 onto the distal end of lead 82. Clamp 94 may be a mechanical clamp, a balloon, or any other suitable mechanism to engage sheath 90 with lead 82 so that lead 82 will move with sheath 90. Balloon 92 is partially inflated and spreads out substantially perpendicular to sheath 90 at sheath tip 91 as shown in FIG. 8A.

Next, as shown in FIG. 8B, balloon 92 is gradually inflated to a higher pressure, causing balloon 92 to expand in the direction indicated by arrow 87. This also causes balloon 92 to press scar tissue 88 and depresses it against heart wall 84, distributing the forces evenly over a larger surface area. This causes lead tip 83 to pull away from heart wall 84 since lead 82 is clamped to sheath 90 with clamp 94. The constant pressure applied by balloon 92 against heart wall 84 provides a traction area of force in the direction indicated by arrow 85 that is opposite the force applied to lead tip 83 of lead 82 in the direction indicated by arrow 87. Due to the cutting of scar tissue 88, and the stabilization achieved by balloon 92 to heart wall 84 around lead tip 83, lead tip 83 is removed with less force than otherwise would be required, thus reducing the likelihood of damage to heart wall 84. This eliminates the need to apply tension over the entire length of lead 82 to remove lead tip 83 from heart wall 84, which in many cases can cause damage to the heart and possible unraveling of lead 82, which can lead to further complications. The force is only applied at the distal end of lead 82 to remove lead tip 83 from heart wall 84 at the point of entry of lead tip 83.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. For example, in the foregoing Detailed Description, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspect, embodiment, and configuration. Thus, the following claims are hereby incorporated into this Detailed Description, with each claim standing on its own as a separate preferred embodiment of the disclosure.

Moreover, though the description of the disclosure has included descriptions of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for lead tip removal by using a device including a sheath having a sheath tip and a stabilization device located at the sheath tip, the method comprising the steps of:
   (a) inserting the sheath over a lead and advancing the sheath to a lead tip attached to a heart wall;
   (b) securing the lead to the sheath;
   (c) applying a first force in a first direction to the heart wall via the stabilization device, wherein the first force simultaneously:
      (c1) stabilizes an area of tissue of the heart wall where the lead tip is attached; and
      (c2) removes the lead tip from the heart wall by producing a second force to displace the lead tip in a second direction relative to the heart wall, the second force being produced by the applying of the first force and being applied to the lead via the sheath, wherein the lead is secured to the sheath, the second direction being opposite the first direction, wherein less force is required to remove the lead tip from the heart wall due to the stabilization provided to the area of tissue of the heart wall by the stabilization device.

2. The method for lead tip removal according to claim 1 wherein the stabilization device is a balloon.

3. The method for lead tip removal according to claim 1 wherein the step (b) comprises engaging a clamp internal to the sheath with the lead to secure the lead to the sheath; and the step (c) comprises inflating a balloon of the stabilization device causing the balloon to expand substantially perpendicular to the lead.

4. The method for lead tip removal according to claim 3 further comprising a step of:
   inflating the balloon to a higher pressure, wherein the balloon expands substantially parallel to the lead, causing the lead tip to pull away from the heart wall.

5. The method for lead tip removal according to claim 3 wherein the step (a) further comprises a step of:
   advancing the sheath over the lead until the sheath tip presses against the balloon and assists the balloon in stabilizing the area of tissue of the heart wall where the lead tip is attached.

6. The method for lead tip removal according to claim 1 wherein the step (a) further comprises a step of:
   cutting through a scar tissue located near the lead tip with a cutting source located in the sheath tip.

* * * * *